(12) United States Patent
Wisbey et al.

(10) Patent No.: US 9,848,828 B2
(45) Date of Patent: Dec. 26, 2017

(54) SYSTEM AND METHOD FOR IDENTIFYING FATIGUE SOURCES

(71) Applicant: LOGITECH EUROPE, S.A., Lausanne (CH)

(72) Inventors: Ben Wisbey, Canberra (AU); David Shepherd, Canberra (AU); Hagen Diesterbeck, Little Bay (NZ); Judd Armstrong, Parrearra (AU)

(73) Assignee: LOGITECH EUROPE, S.A., Lausanne (CH)

( * ) Notice: Subject to any disclaimer, the term of this patent is extended or adjusted under 35 U.S.C. 154(b) by 362 days.

(21) Appl. No.: 14/259,725

(22) Filed: Apr. 23, 2014

(65) Prior Publication Data

US 2015/0120203 A1 Apr. 30, 2015

Related U.S. Application Data

(63) Continuation-in-part of application No. 14/147,384, filed on Jan. 3, 2014, which is a continuation-in-part of application No. 14/137,942, filed on Dec. 20, 2013, which is a continuation-in-part of application No. 14/137,734, filed on Dec. 20, 2013, which is a continuation-in-part of application No. 14/062,815, filed on Oct. 24, 2013.

(51) Int. Cl.
*G08C 19/16* (2006.01)
*A61B 5/00* (2006.01)
*A61B 5/11* (2006.01)

(52) U.S. Cl.
CPC .......... *A61B 5/7275* (2013.01); *A61B 5/1118* (2013.01); *A61B 5/4812* (2013.01); *A61B 5/4815* (2013.01); *A61B 5/681* (2013.01); *A61B 5/6826* (2013.01); *A61B 5/1112* (2013.01)

(58) Field of Classification Search
CPC ...... A61L 5/4812; A61L 5/681; A61L 5/6826; A61L 5/1118; A61L 5/4815; A61L 5/7275; A61L 5/1112
See application file for complete search history.

(56) References Cited

U.S. PATENT DOCUMENTS

| | | |
|---|---|---|
| 2,189,096 A | 2/1940 | Alonge |
| 3,543,724 A | 12/1970 | Kirkpatrick et al. |
| 3,978,849 A | 9/1976 | Geneen |
| 4,129,124 A | 12/1978 | Thalmann |

(Continued)

OTHER PUBLICATIONS

"Elite Clock Military Style LED Watch" by ledwatchsuk. YouTube [dated May 31, 2011][online][retrieved on Aug. 14, 2015].

(Continued)

*Primary Examiner* — Quang D Pham
(74) *Attorney, Agent, or Firm* — Pattersons & Sheridan, LLP

(57) ABSTRACT

A system for identifying fatigue sources includes a processor and at least one computer program residing on the processor. The computer program is stored on a non-transitory computer readable medium having computer executable code embodied thereon. The computer executable code is configured to detect a fatigue level. The computer executable code is further configured to receive fatigue contribution data. In addition, the computer executable code is configured to identify a fatigue source based on the fatigue level and the fatigue contribution data.

10 Claims, 9 Drawing Sheets

(56) References Cited

U.S. PATENT DOCUMENTS

| | | |
|---|---|---|
| 4,224,948 A | 9/1980 | Cramer et al. |
| 4,307,727 A | 12/1981 | Haynes |
| 4,331,154 A | 5/1982 | Broadwater et al. |
| 4,407,295 A | 10/1983 | Steuer et al. |
| 4,409,983 A | 10/1983 | Albert |
| 4,491,970 A | 1/1985 | LaWhite et al. |
| 5,301,154 A | 4/1994 | Suga |
| 5,392,261 A | 2/1995 | Hsu |
| 5,406,952 A | 4/1995 | Barnes et al. |
| 5,524,637 A | 6/1996 | Erickson |
| 5,734,625 A | 3/1998 | Kondo |
| 5,755,623 A | 5/1998 | Mizenko |
| 5,899,370 A | 5/1999 | Bould |
| 6,151,968 A | 11/2000 | Chou |
| 6,361,503 B1 | 3/2002 | Starobin et al. |
| 6,736,759 B1 | 5/2004 | Stubbs et al. |
| 7,192,401 B2 | 3/2007 | Saalasti et al. |
| 7,717,827 B2 | 5/2010 | Kurunmaki et al. |
| 7,914,425 B2 | 3/2011 | Hanoun |
| 8,821,417 B2* | 9/2014 | McGregor ............ A61B 5/1118 600/587 |
| 8,992,385 B2 | 3/2015 | Lemos |
| 2002/0007105 A1* | 1/2002 | Prabhu ................. A61M 21/00 600/26 |
| 2002/0017994 A1* | 2/2002 | Balkin .................... A61B 5/16 340/573.1 |
| 2002/0151811 A1 | 10/2002 | Starobin et al. |
| 2002/0188210 A1 | 12/2002 | Aizawa |
| 2003/0065269 A1 | 4/2003 | Vetter et al. |
| 2005/0056655 A1 | 3/2005 | Gary |
| 2005/0116811 A1 | 6/2005 | Eros et al. |
| 2005/0256416 A1 | 11/2005 | Chen |
| 2006/0079800 A1* | 4/2006 | Martikka ............. A61B 5/0488 600/546 |
| 2006/0183980 A1 | 8/2006 | Yang |
| 2006/0200008 A1* | 9/2006 | Moore-Ede ............ B60K 28/06 600/300 |
| 2006/0247542 A1* | 11/2006 | Watanabe ................ A61B 5/16 600/500 |
| 2007/0118043 A1 | 5/2007 | Oliver et al. |
| 2008/0086318 A1 | 4/2008 | Gilley et al. |
| 2008/0132383 A1 | 6/2008 | Einav et al. |
| 2008/0228089 A1 | 9/2008 | Cho et al. |
| 2009/0066521 A1* | 3/2009 | Atlas ........................ A61B 5/18 340/575 |
| 2009/0312656 A1 | 12/2009 | Lau et al. |
| 2009/0322513 A1* | 12/2009 | Hwang ............. A61B 5/02055 340/539.12 |
| 2010/0137748 A1* | 6/2010 | Sone ..................... A61B 5/1118 600/595 |
| 2010/0197463 A1 | 8/2010 | Haughay, Jr. et al. |
| 2011/0021319 A1 | 1/2011 | Nissila et al. |
| 2011/0092790 A1 | 4/2011 | Wilder-Smith et al. |
| 2011/0161227 A1* | 6/2011 | Santo, Jr. ................ G06Q 10/10 705/40 |
| 2011/0190645 A1* | 8/2011 | Hunt ..................... A61B 5/0205 600/500 |
| 2011/0257542 A1* | 10/2011 | Russell ................. A61B 5/0205 600/500 |
| 2011/0260870 A1 | 10/2011 | Bailey |
| 2011/0288424 A1* | 11/2011 | Kanai ....................... A61B 5/18 600/500 |
| 2012/0022341 A1 | 1/2012 | Zdeblick |
| 2012/0078063 A1* | 3/2012 | Moore-Ede ............ B60K 28/06 600/300 |
| 2012/0089553 A1* | 4/2012 | Mollicone ........... G06F 19/3431 706/52 |
| 2012/0168471 A1 | 7/2012 | Wilson |
| 2012/0203464 A1* | 8/2012 | Mollicone .......... G06Q 10/0639 702/19 |
| 2012/0253485 A1 | 10/2012 | Weast et al. |
| 2013/0064049 A1 | 3/2013 | Pileri et al. |
| 2013/0110011 A1* | 5/2013 | McGregor ............ A61B 5/1118 600/595 |
| 2013/0123669 A1* | 5/2013 | Kinoshita ............... A61B 5/112 600/595 |
| 2013/0144181 A1* | 6/2013 | Fogt ................. A61B 5/02405 600/521 |
| 2013/0236978 A1* | 9/2013 | Kalns ................. G01N 33/6893 436/86 |
| 2013/0237775 A1* | 9/2013 | Gross ................... A61B 5/0205 600/301 |
| 2013/0237778 A1 | 9/2013 | Rouquette |
| 2014/0032234 A1 | 1/2014 | Anderson |
| 2014/0073486 A1 | 3/2014 | Ahmed et al. |
| 2014/0077955 A1* | 3/2014 | Hollender .............. G08B 21/02 340/573.1 |
| 2014/0107493 A1 | 4/2014 | Yuen et al. |
| 2014/0156084 A1* | 6/2014 | Rahman ................. A61B 5/681 700/276 |
| 2014/0228175 A1 | 8/2014 | Lemos et al. |
| 2015/0026351 A1* | 1/2015 | Calman ............... H04L 65/1083 709/227 |
| 2015/0186609 A1* | 7/2015 | Utter, II ............... A61B 5/0022 600/301 |

OTHER PUBLICATIONS

"Watch Stylish Blue Light LED Round Dial Matrix Stainless from ChinaBuye.com" by YnopoB. YouTube [dated Apr. 23, 2012][online][retrieved on Dec. 31, 2015] (https://www.youtube.com/watch?v=e_LWbXHvvWg).

\* cited by examiner

SYSTEM AND METHOD FOR IDENTIFYING FATIGUE SOURCES

CROSS-REFERENCE TO RELATED APPLICATIONS

This application is a continuation-in-part of and claims the benefit of U.S. patent application Ser. No. 14/147,384, filed Jan. 3, 2014, titled "System and Method for Providing Sleep Recommendations," which is a continuation-in-part of U.S. patent application Ser. No. 14/137,942, filed Dec. 20, 2013, titled "System and Method for Providing an Interpreted Recovery Score," which is a continuation-in-part of U.S. patent application Ser. No. 14/137,734, filed Dec. 20, 2013, titled "System and Method for Providing a Smart Activity Score," which is a continuation-in-part of U.S. patent application Ser. No. 14/062,815, filed Oct. 24, 2013, titled "Wristband with Removable Activity Monitoring Device." The contents of the application Ser. No. 14/147,384, the application Ser. No. 14/137,942, the application Ser. No. 14/137,734, and the application Ser. No. 14/062,815 are incorporated herein by reference.

TECHNICAL FIELD

The present disclosure relates generally to fitness monitoring devices, and more particularly to a system and method for identifying fatigue sources.

DESCRIPTION OF THE RELATED ART

Previous generation fitness monitoring devices generally enabled only a tracking of activity and fatigue that accounts for total calories burned. Currently available fitness monitoring devices now add functionality that tracks activity and fatigue based on universal metabolic equivalent tasks. One issue is that currently available fitness monitoring devices do not identify when a user is fatigued based on biological, scientific metrics. Moreover, currently available solutions do not provide a way to identify the source of a user's fatigue. Another issue is that currently available solutions do not rank the sources of the user's fatigue, and thus do not enable the user to make informed lifestyle choices that will help the user achieve balance.

BRIEF SUMMARY OF THE DISCLOSURE

In view of the above drawbacks, there exists a long-felt need for fitness monitoring devices that detect a fatigue level in a scientific way and identify the sources of the user's fatigue, or fatigue sources. Further, there is a need for fitness monitoring devices that rank the user's identified fatigue sources to provide insight into how the user may achieve a more balanced lifestyle, optimize fatigue, and maximize performance.

Embodiments of the present disclosure include systems and methods for identifying fatigue sources. One embodiment of the disclosure includes a system for identifying fatigue sources. The system includes a processor and at least one computer program residing on the processor. The computer program is stored on a non-transitory computer readable medium having computer executable program code embodied thereon. At least a portion of the computer readable medium, in one embodiment, is embodied in a wearable sensor.

The computer executable program code is configured to detect a fatigue level. The computer executable program code is further configured to receive fatigue contribution data. In addition, the computer executable program code is configured to identify a fatigue source based on the fatigue level and the fatigue contribution data. The fatigue source, in one embodiment, is identified further based on user input. In one embodiment, the computer executable code is further configured to prompt a user to provide the user input. In one scenario, the fatigue source includes at least one of an activity type, an activity intensity, an activity duration, and an activity periodicity.

The fatigue contribution data, in one embodiment of the system, includes activity data. In an additional embodiment, the activity data is associated with at least one of an activity type, an activity intensity, an activity duration, and an activity periodicity. The fatigue contribution data, in one instance, includes sleep data, which is associated with at least one of a sleep duration, a sleep timing, a sleep quality, and an ambient light. In one case, the fatigue contribution data includes location data. The location data, in a further embodiment, is associated with at least one of a GPS location, an altitude, and an ambient temperature. In an additional embodiment of the disclosure, the fatigue contribution data includes calendar data.

One embodiment of the present disclosure involves a method for identifying fatigue sources. The method includes detecting a fatigue level. The method also includes receiving fatigue contribution data. In addition, the method includes identifying a fatigue source based on the fatigue level and the fatigue contribution data. The method, in one embodiment, includes capturing the fatigue contribution data. The fatigue contribution data, in one instance, is associated with fatigue contribution parameters.

In one embodiment of the disclosure, the method includes maintaining historical information about the fatigue levels, the fatigue contribution parameters, and the fatigue sources. Another embodiment includes displaying temporal trends in the historical information. Identifying the fatigue source, in an additional embodiment, includes creating and updating a fatigue profile based on the historical information and comparing the fatigue level and the fatigue contribution data to the fatigue profile. In one instance, the method includes receiving user confirmation of identified fatigue sources. In another instance, the method includes ranking multiple fatigue sources.

One embodiment of the disclosure involves an apparatus for identifying fatigue sources. The apparatus includes a fatigue level module that detects a fatigue level. The apparatus also includes a fatigue contribution module that receives fatigue contribution data. In addition, the apparatus includes a fatigue source module that identifies a fatigue source based on the fatigue level and the fatigue contribution data.

Other features and aspects of the disclosure will become apparent from the following detailed description, taken in conjunction with the accompanying drawings, which illustrate, by way of example, the features in accordance with embodiments of the disclosure. The summary is not intended to limit the scope of the disclosure, which is defined solely by the claims attached hereto.

BRIEF DESCRIPTION OF THE DRAWINGS

The present disclosure, in accordance with one or more various embodiments, is described in detail with reference to the following figures. The figures are provided for purposes of illustration only and merely depict example embodiments of the disclosure.

The figures are not intended to be exhaustive or to limit the disclosure to the precise form disclosed. It should be understood that the disclosure can be practiced with modification and alteration, and that the disclosure can be limited only by the claims and the equivalents thereof.

DETAILED DESCRIPTION

The present disclosure is directed toward systems and methods for identifying fatigue sources and various embodiments of such systems and methods. In one such embodiment, the systems and methods are directed to a device that identifies fatigue sources. According to some embodiments of the disclosure, the device may be an electronic capsule embedded in and removable from an attachable device that may be attached to a user. In one embodiment, the attachable device is a wristband. The attachable device may include or be part of a fitness or activity monitoring device.

Figure 1:
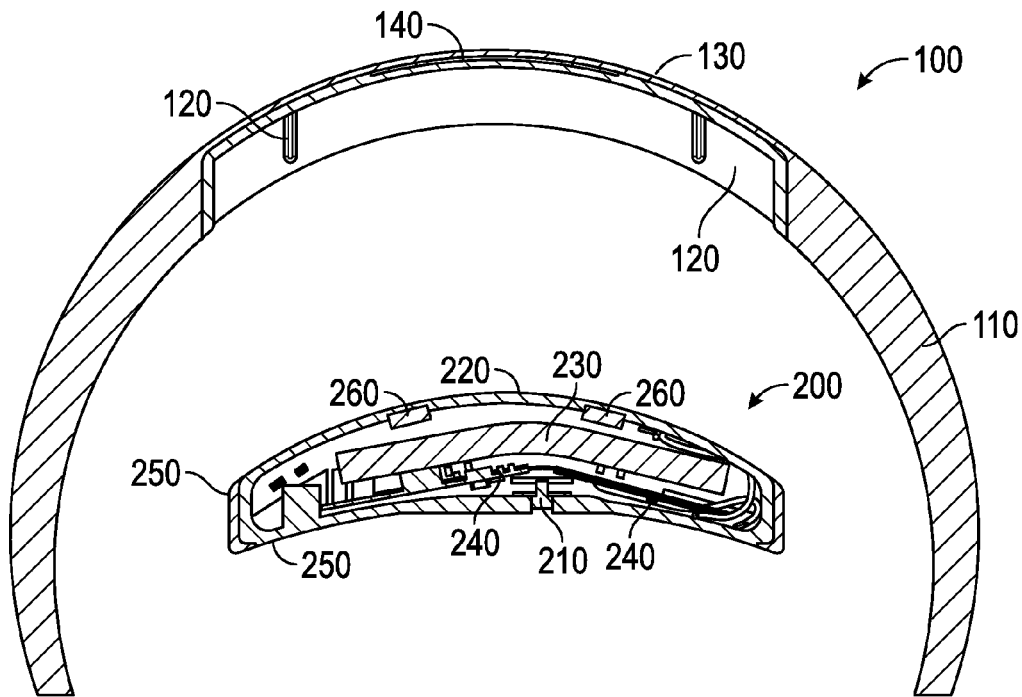
FIG. 1 illustrates a cross-sectional view of a wristband and electronic modules of an example fitness and activity monitoring device.

FIG. 1 is a diagram illustrating a cross-sectional view of an example embodiment of an activity monitoring device. Referring now to FIG. 1, an activity monitoring device comprises electronic capsule 200 and wristband 100. Electronic capsule 200 comprises wrist biosensor 210, finger biosensor 220, battery 230, one or more logic circuits 240, and casing 250.

In some embodiments, one or more logic circuits 240 comprise an accelerometer, a wireless transmitter, a wireless receiver, and circuitry. Logic circuits 240 may further comprise a gyroscope. Logic circuits 240 may be configured to process electronic input signals from biosensors 210, 220 and the accelerometer, store the processed signals as data, and output the data using the wireless transmitter. The transmitter is configured to communicate using available wireless communications standards (e.g., over communication medium 704). For example, in some embodiments, the wireless transmitter is a BLUETOOTH transmitter, a Wi-Fi transmitter, a GPS transmitter, a cellular transmitter, or a combination thereof. In an alternative embodiment, the wireless transmitter further comprises a wired interface (e.g. USB, fiber optic, HDMI, etc.) for communicating stored data.

Logic circuits 240 are electrically coupled to wrist biosensor 210 and finger biosensor 220. In addition, logic circuits 240 are configured to receive and process a plurality of electric signals from each of wrist biosensor 210 and finger biosensor 220. In some embodiments, the plurality of electric signals includes an activation time signal and a recovery time signal such that logic circuits 240 process the plurality of signals to calculate an activation recovery interval equal to the difference between the activation time signal and the recovery time signal. In some embodiments, the plurality of signals include electro-cardio signals from a heart, and logic circuits 240 process the electro-cardio signals to calculate and store an RR-interval, and the RR-interval is used to calculate and store a heart rate variability (HRV) value. In such embodiments, the RR-interval is equal to the delta in time between two R-waves, where the R-waves are the electro-cardio signals generated by a ventricle contraction in the heart.

In some embodiments, logic circuits 240 further detect and store metrics such as the amount of physical activity, sleep, or rest over a recent period of time, or the amount of time without physical activity over a recent period of time. Logic circuits 240 may then use the HRV, or the HRV in combination with these metrics, to calculate a fatigue level. For example, logic circuits 240 may detect the amount of physical activity and the amount of sleep a user experienced over the last 48 hours, combine those metrics with the user's HRV, and calculate a fatigue level of between 1 and 10. In such an example, the fatigue level may indicate the user's physical condition and aptitude for further physical activity that day. The fatigue level may also be calculated on a scale of between 1 and 100, or any other scale or range. In addition, the fatigue level may be represented on a descriptive scale—for example, low, normal, and high.

Finger biosensor 220 and wrist biosensor 210, in some embodiments, are replaced or supplemented by a single biosensor. In one such embodiment, the single biosensor is an optical biosensor such as a pulse oximeter configured to detect blood oxygen saturation levels. The pulse oximeter may then output a signal to logic circuits 240 indicating a detected cardiac cycle phase, and logic circuits 240 may use cardiac cycle phase data to calculate an HRV value.

Wristband 100 comprises material 110 configured to encircle a human wrist. In one embodiment, wristband 100 is adjustable. Cavity 120 is notched on the radially inward facing side of wristband 100 and shaped to substantially the same dimensions as the profile of electronic capsule 200. In addition, aperture 130 is located in material 110 within cavity 120. Aperture 130 is shaped to substantially the same dimensions as the profile of finger biosensor 220. The combination of cavity 120 and aperture 130 is designed to detachably couple to electronic capsule 200 such that, when electronic capsule 200 is positioned inside cavity 120, finger biosensor 220 protrudes through aperture 130. Electronic capsule 200 may further comprise one or more magnets 260 configured to secure electronic capsule 200 to cavity 120. Magnets 260 may be concealed in casing 250. Cavity 120 may be configured to conceal magnets 260 when electric capsule 200 detachably couples to the combination of cavity 120 and aperture 130.

Wristband 100 may further comprise steel strip 140 concealed in material 110 within cavity 120. In this embodiment, when electronic capsule 200 is positioned within cavity 120, one or more magnets 260 are attracted to steel strip 140 and pull electronic capsule 200 radially outward with respect to wristband 100. The force provided by magnets 260 may detachably secure electronic capsule 200 inside cavity 120. In further embodiments, electronic capsule 200 is positioned inside cavity 120 and affixed using a form-fit, press-fit, snap-fit, friction-fit, VELCRO, or other temporary adhesion or attachment technology.

Figure 2:
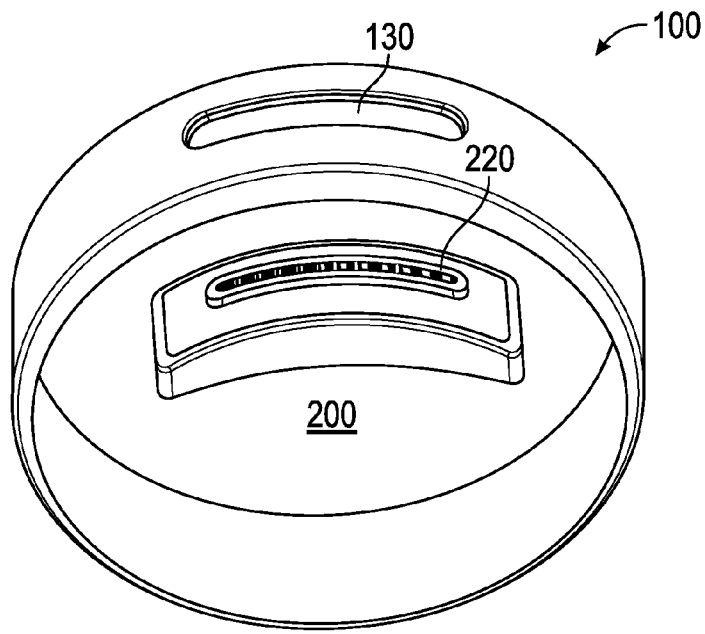
FIG. 2 illustrates a perspective view of an example fitness and activity monitoring device.
Figure 3:
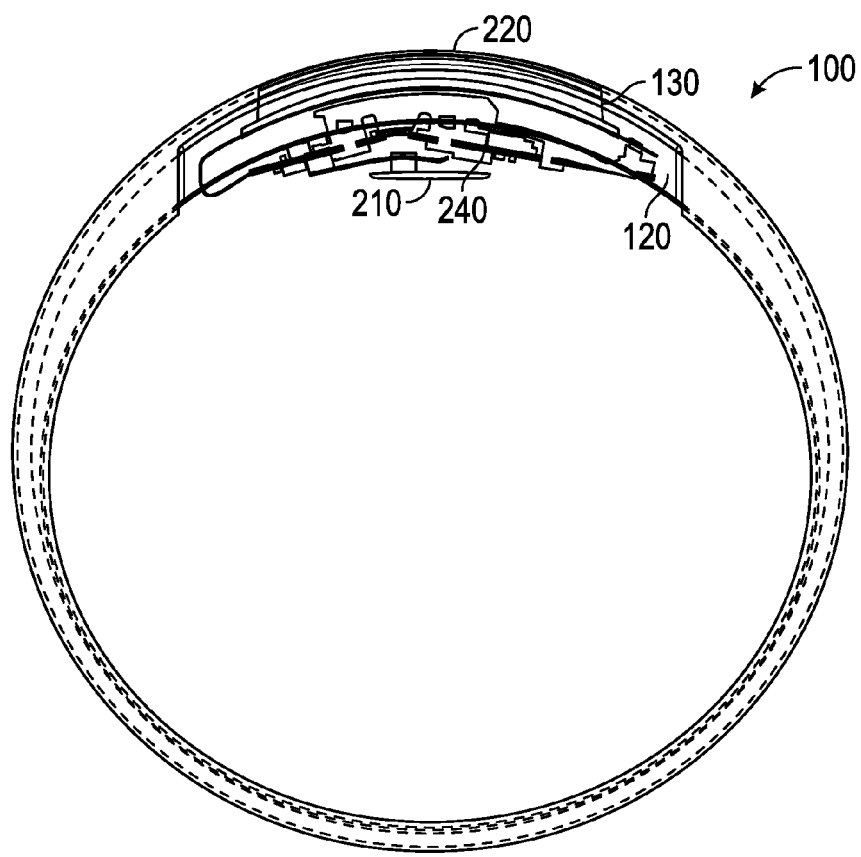
FIG. 3 illustrates a cross-sectional view of an example assembled fitness and activity monitoring device.
Figure 4:
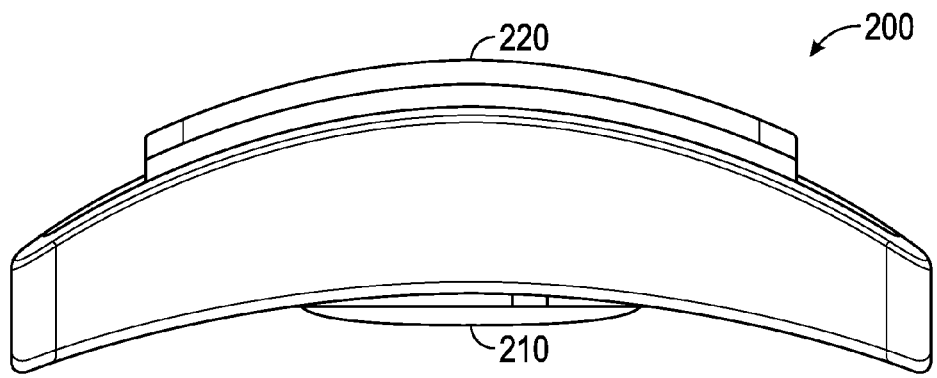
FIG. 4 illustrates a side view of an example electronic capsule.
Figure 5:
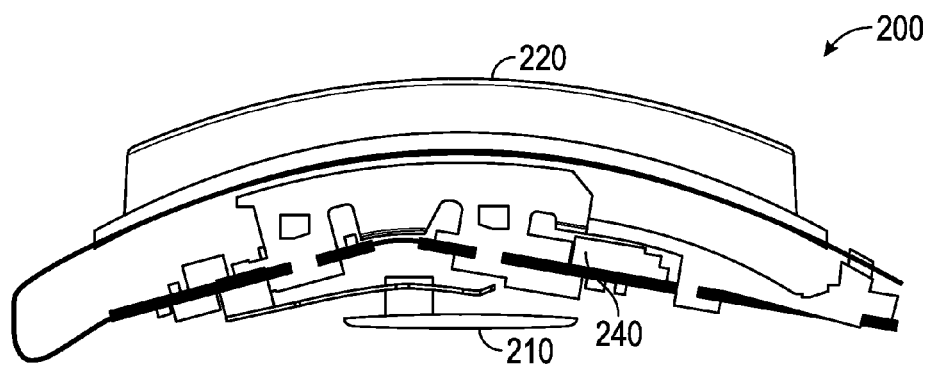
FIG. 5 illustrates a cross-sectional view of an example electronic capsule.
Figure 6:
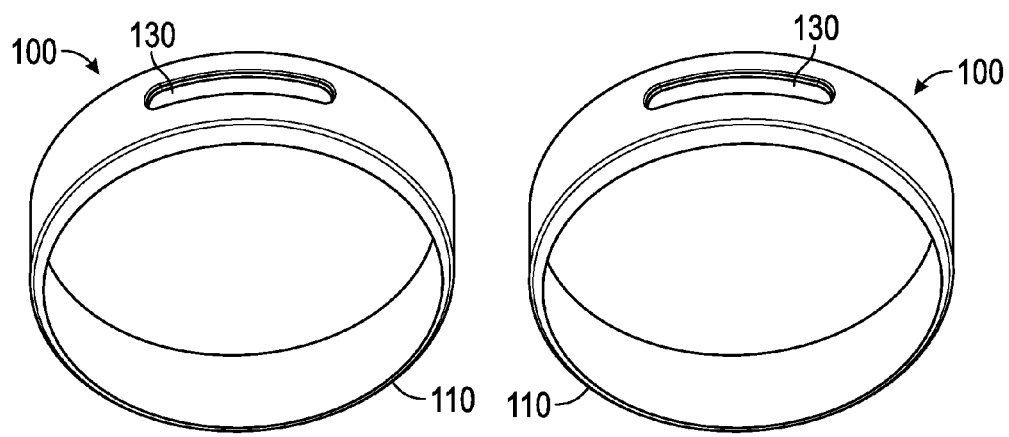
FIG. 6 illustrates perspective views of wristbands as used in one embodiment of the disclosure.

FIG. 2 illustrates a perspective view of one embodiment of the disclosed activity monitoring device, which may include the device for identifying fatigue sources. In FIG. 2, wristband 100 and electronic capsule 200 are unassembled. FIG. 3 illustrates a cross-sectional view of one embodiment of a fully assembled wristband 100 with removable activity monitoring device. FIG. 4 illustrates a side view of electronic capsule 200 according to one embodiment of the disclosure. FIG. 5 illustrates a cross-sectional view of electronic capsule 200. FIG. 6 is a perspective view of two possible variants of wristband 100 according to some embodiments of the disclosure. Wristbands 100 may be constructed with different dimensions, including different diameters, widths, and thicknesses, in order to accommodate different human wrist sizes and different preferences.

In some embodiments of the disclosure, electronic capsule 200 is detachably coupled to a cavity on a shoe and/or a sock. In other embodiments, electronic capsule 200 is detachably coupled to sports equipment. For example, electronic capsule 200 may be detachably coupled to a skateboard, a bicycle, a helmet, a surfboard, a paddle boat, a body board, a hang glider, or other piece of sports equipment. In these embodiments, electronic capsule 200 is affixed to the sports equipment using magnets. In other embodiments, electronic capsule 200 is affixed using a form-fit, snap-fit, press-fit, friction-fit suction cup, VELCRO, or other technology that would be apparent to one of ordinary skill in the art.

In one embodiment of the disclosure, electronic capsule 200 includes an optical sensor such as a heart rate sensor or oximeter. In this embodiment, the optical sensor is positioned to face radially inward towards a human wrist when wristband 100 is fit on the human wrist. The optical sensor, in another example, is separate from electronic capsule 200, but is still detachably coupled to wristband 100 and electronically coupled to the circuit boards enclosed in electronic capsule 200. Wristband 100 and electronic capsule 200 may operate in conjunction with a system for identifying fatigue sources.

Figure 7:
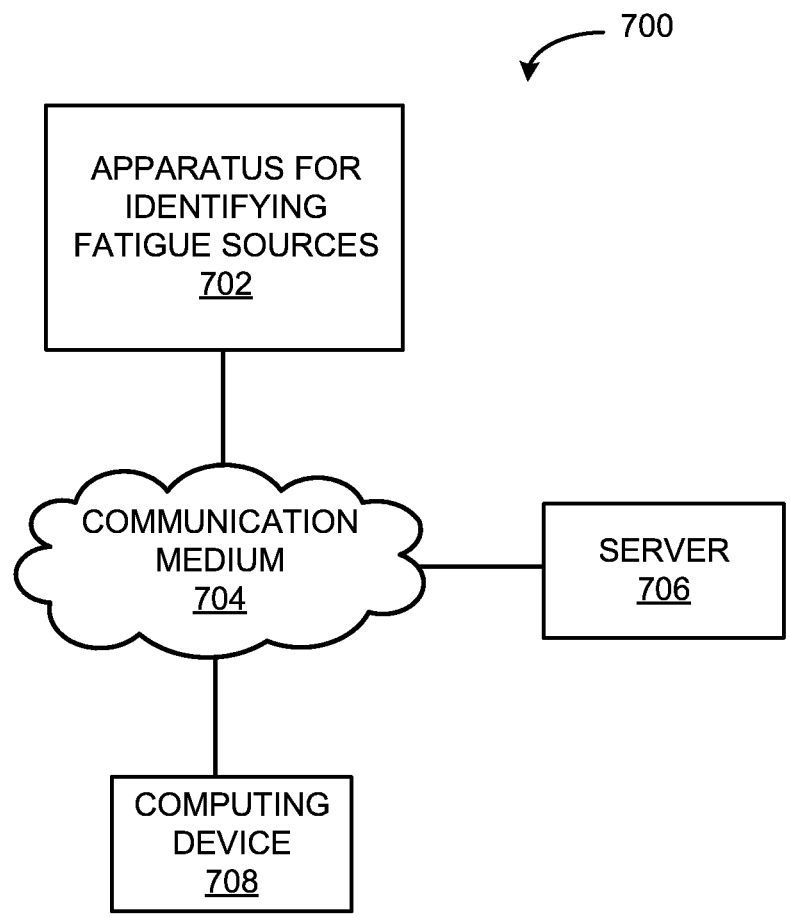
FIG. 7 illustrates an example system for identifying fatigue sources.

FIG. 7 is a schematic block diagram illustrating example system 700 for identifying fatigue sources. System 700 includes apparatus for identifying fatigue sources 702, communication medium 704, server 706, and computing device 708.

Communication medium 704 may be implemented in a variety of forms. For example, communication medium 704 may be an Internet connection, such as a local area network ("LAN"), a wide area network ("WAN"), a fiber optic network, internet over power lines, a hard-wired connection (e.g., a bus), and the like, or any other kind of network connection. Communication medium 704 may be implemented using any combination of routers, cables, modems, switches, fiber optics, wires, radio, and the like. Communication medium 704 may be implemented using various wireless standards, such as Bluetooth, Wi-Fi, 4G LTE, etc. One of skill in the art will recognize other ways to implement communication medium 704 for communications purposes.

Server 706 directs communications made over communication medium 704. Server 706 may be, for example, an Internet server, a router, a desktop or laptop computer, a smartphone, a tablet, a processor, a module, or the like. In one embodiment, server 706 directs communications between communication medium 704 and computing device 708. For example, server 706 may update information stored on computing device 708, or server 706 may send information to computing device 708 in real time.

Computing device 708 may take a variety of forms, such as a desktop or laptop computer, a smartphone, a tablet, a processor, a module, or the like. In addition, computing device 708 may be a processor or module embedded in a wearable sensor, a bracelet, a smart-watch, a piece of clothing, an accessory, and so on. For example, computing device 708 may be substantially similar to devices embedded in electronic capsule 200, which may be embedded in and removable from wristband 100, as illustrated in FIG. 1. Computing device 708 may communicate with other devices over communication medium 704 with or without the use of server 706. In one embodiment, computing device 708 includes apparatus 702. In various embodiments, apparatus 702 may be used to perform various processes described herein. One of skill in the art will appreciate, however, that the various processes described herein may be performed on the device side (e.g., by apparatus 702 or computing device 708) or on the server side (e.g., by one or more computers coupled to server 706).

Figure 8:
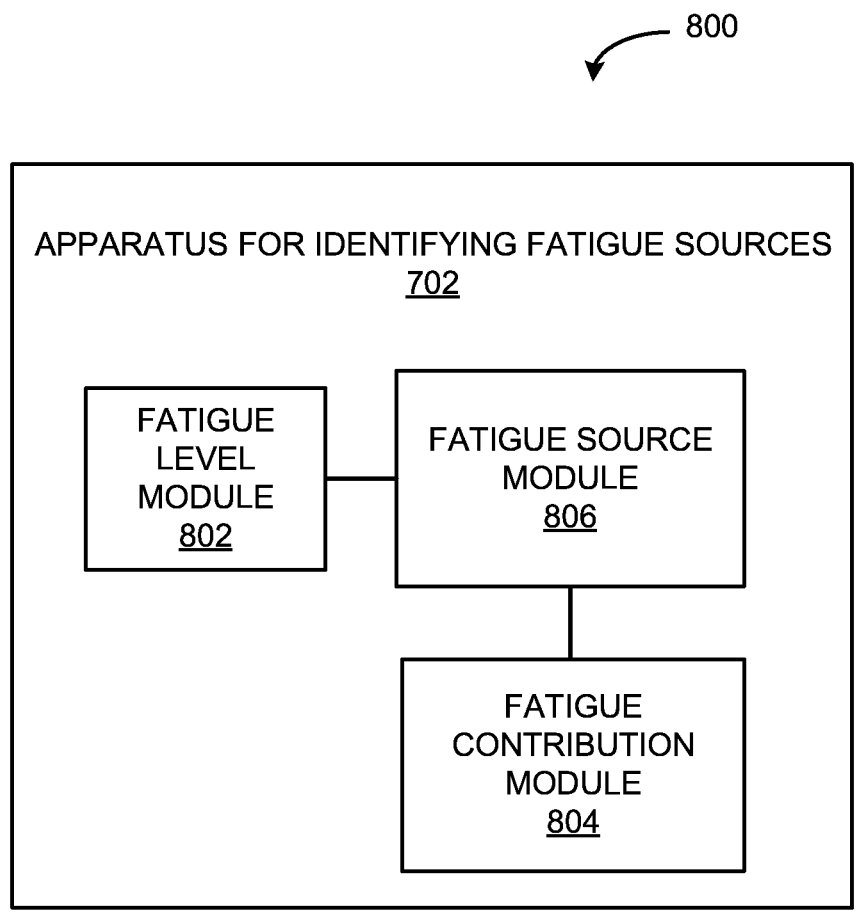
FIG. 8 illustrates an example apparatus for identifying fatigue sources.

FIG. 8 is a schematic block diagram illustrating one embodiment of apparatus for identifying fatigue sources 800. Apparatus 800 includes apparatus 702 with fatigue level module 802, fatigue contribution module 804, and fatigue source module 806. Fatigue level module 802 detects a fatigue level. Fatigue contribution module 804 receives fatigue contribution data. Fatigue source module 806 identifies a fatigue source based on the fatigue level and the fatigue contribution data. Fatigue level module 802, fatigue contribution module 804, and fatigue source module 806 will be described below in further detail with regard to various processes. In one embodiment, at least one of fatigue level module 802, fatigue contribution module 804, and fatigue source module 806 is embodied in a wearable sensor, such as electronic capsule 200. In various embodiments, any of the modules described herein are embodied in electronic capsule 200 and connect to other modules described herein via communication medium 704.

Figure 9:
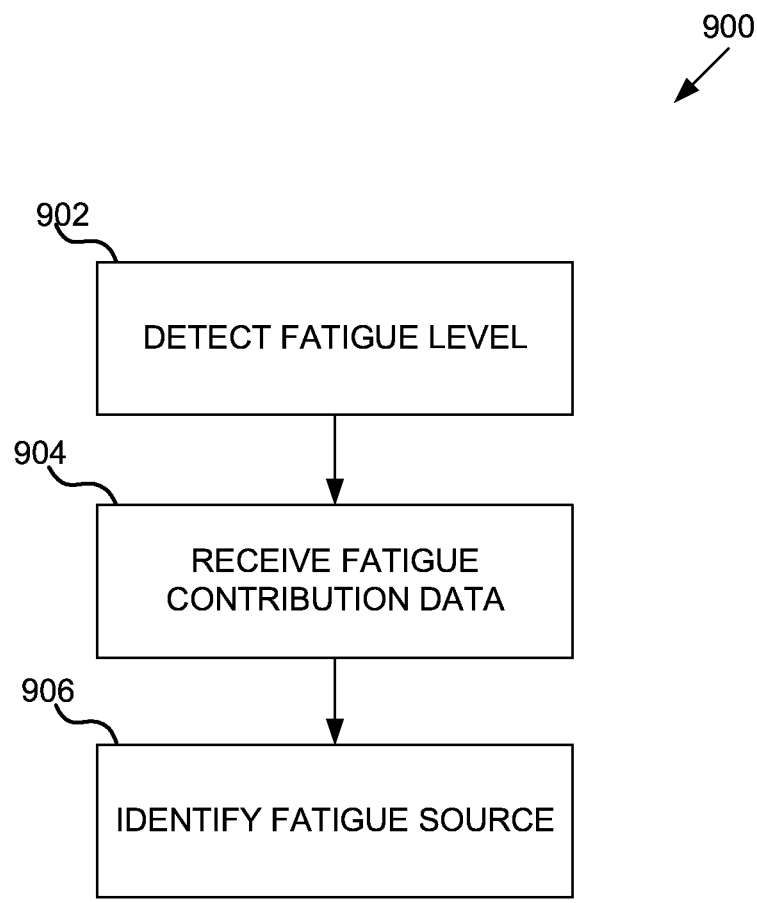
FIG. 9 is an operational flow diagram illustrating an example method for identifying fatigue sources.

FIG. 9 is an operational flow diagram illustrating example method 900 for identifying fatigue sources in accordance with the present disclosure. In addition to identifying that a user is fatigued based on the user's scientifically detected fatigue level (e.g., by measuring HRV), the operations of method 900 provide insight as to the causes of the user's fatigue. This aids the user in making informed decisions about the user's lifestyle and health, including maintaining stress and work levels, exercise levels, and sleep schedules. In one embodiment, apparatus 702, wristband 100, and electronic capsule 200 perform various operations of method 900.

At operation 902, method 900 involves detecting a fatigue level of a user. The fatigue level may be a function of recovery and may be described in terms of recovery. The fatigue level may be detected in various ways. In one example, the fatigue level is detected by measuring a heart rate variability (HRV) of the user using logic circuits 240 (discussed above in reference in to FIG. 1). Further, possible representations of the fatigue level are described above (e.g., numerical, descriptive, etc.). When the HRV is more consistent (i.e., steady, consistent amount of time between heartbeats), for example, the fatigue level may be higher. In other words, with a higher fatigue level, the body is typically less fresh and less well-rested. When HRV is more sporadic (i.e., amount of time between heartbeats varies largely), the fatigue level may be lower. In various embodiments, the fatigue level is described in terms of an HRV score.

HRV may be measured in a number of ways (discussed above in reference in to FIG. 1). Measuring HRV, in one embodiment, involves the combination of wrist biosensor 210 and finger biosensor 220. Wrist biosensor 210 may measure the heartbeat in the wrist of one arm while finger sensor 220 measures the heartbeat in a finger of the hand of the other arm. This combination allows the sensors, which in one embodiment are conductive, to measure an electrical potential through the body. Information about the electrical potential provides cardiac information (e.g., HRV, fatigue level, heart rate information, and so on), and such information may be processed at operation 1004. In other embodiments, the HRV is measured using sensors that monitor other parts of the user's body, rather than the finger and wrist. For example, the sensors may monitor the ankle, leg, arm, or torso.

At operation 904, method 900 involves receiving fatigue contribution data. The fatigue contribution data may include many different types of information. In one embodiment, the fatigue contribution data includes activity data. Activity data may, for example, represent activity type, activity intensity, activity duration, activity periodicity, and activity timing. The activity data may be determined using a movement monitoring device; for example, a gyroscope and/or accelerometer.

Various activities that the user may perform may be represented categorically by activity type. Potential activity types may include typical activities, such as running, walking, sleeping, swimming, bicycling, skiing, surfing, resting, working, and so on. Activity types may also include a catch-all category, for example, general exercise. User activities may also be represented in terms of activity intensity. The activity intensity is represented, in one embodiment, on a numeric scale. By way of example, the activity intensity may be a number between one and ten, and may be associated with the vigorousness of the activity. For example, the reference activity intensities may be represented by ranges of heart rates or breathing rates. Activity duration, in one embodiment, is defined in terms of activity type—i.e., the length of time for which a particular activity type was performed. Activity duration may also be defined more specifically. For example, activity duration may be defined as the length of time for which a particular activity type was performed at a particular activity intensity. Activity periodicity, in one embodiment, represents how often the user performs a particular activity type—e.g., the activity periodicity for running may be three times per week. Activity timing may represent for example the time of day at which the user performed the activity type.

Activity data may be determined by monitoring the user's movement, which, in one embodiment, is accomplished using sensors configured to be attached to the user's body. Such sensors may include a gyroscope or accelerometer to detect movement, and a heart-rate sensor, each of which may be embedded in a wristband that a user can wear on the user's wrist or ankle, such as wristband 100. Additionally, various modules and sensors that may be used to perform the above-described operations may be embedded in electronic capsule 200. In various embodiments, the above-described operations are performed by a movement monitoring module (not shown).

Certain activity types, activity intensities, activity durations, or activity periodicities may result in high fatigue levels. The activity types, activity intensities, activity durations, and activity periodicities that cause high fatigue levels may be user-specific. For example, a particular user may become highly fatigued by running but not by swimming. As a further example, another user may become highly fatigued by swimming but not running. Similarly, high activity intensities may result in disproportionately high fatigue levels that are not beneficial to the user. Because the relationship between these various activity elements is monitored specifically for the user, one benefit of the disclosure is to provide the user information about how the user may better balance the user's lifestyle according to the user's biologically preferred activities (as indicated by the fatigue level).

In one embodiment, the fatigue contribution data received at operation 904 includes sleep data, which represents various aspects of the user's sleep activities. Sleep data may represent sleep duration, sleep timing, sleep quality, ambient light conditions during the sleep duration, and other characteristics of the user's sleep. The sleep data may be determined using a movement monitoring device; for example, a gyroscope and/or accelerometer. The sleep data may also include information entered by the user.

Sleep duration may include the amount of time the user sleeps during the night, or during a nap. This may be monitored by a movement monitoring device. Sleep timing may include the time at which sleep begins or ends. Sleep quality, in one embodiment, represents the restfulness of the user's sleep. Sleep quality may depend on such factors as movement during sleep, sleep duration, sleep timing, and ambient lighting during sleep. By way of example, the sleep quality may be a number between one and ten. Ambient light may be detected by a sensor on the movement monitoring device or on wristband 100, and may affect the user's sleep quality or fatigue level. The sleep data may also include information entered by the user. For example, the user may enter that the user had high-quality sleep for 8 hours, starting at 10:00 PM.

In one embodiment, the fatigue contribution data includes location data. Location data may contribute to fatigue for various reasons. For example, location data may indicate that the user is travelling, which in and of itself may cause fatigue. Location data may indicate that the user is in abnormal conditions, whether such conditions be related to weather, activity generally, work, and so on. Such abnormalities may affect the user's fatigue level.

Location data may include the actual location of the user, but may also include information about the user's environment. For example, the location data may represent GPS coordinates, a city, a zip code, etc.; may be associated with an altitude or elevation; and may be associated with an ambient temperature. Moreover, the location data may include information about other weather conditions, including humidity, pollen content, pollution, and so on. Such information, including ambient temperature, may be measured by sensors (e.g., on wristband 100 or on a movement monitoring device). In some cases, information about altitude, temperature, humidity, and other weather conditions may be collected from external sources based on the user's location. For example, if the user's location is determined to be in Astoria, Oreg., information about conditions associated with that city may be collected via communication medium 704.

The fatigue contribution data, in a further embodiment, includes calendar data. Calendar data may include the nature, duration, and frequency of entries on one or more of the user's calendars, and may be received via communication medium 704. In one embodiment, calendar data is a proxy for detected activity types and durations. For example, if the user's calendar says that the user went running for one hour on Wednesday, this may substitute for activity data. In addition, the calendar may serve as a check or supplement to the activity data. Moreover, calendar data may indicate how much the user is working, and the frequency and nature of various activities may indicate the user's stress level. For example, if the calendar data includes many entries on a to-do list, the user may be experiencing higher stress levels.

The fatigue contribution data, in one embodiment, is associated with fatigue contribution parameters. Fatigue contribution parameters may represent a quantified value for fatigue contribution data. For example, one fatigue contribution parameter may be activity intensity, which may be represented on a numerical scale from 1 to 10. Another example of a fatigue contribution parameter is sleep duration, which may be represented in terms of minutes, seconds, and so on. In general, the fatigue contribution parameters include or are defined in terms of all the various types of data, measurements, or inputs that may affect the user's fatigue level. Fatigue contribution parameters, in one embodiment, encompass activity data, sleep data, location data, calendar data, and the like. In addition, fatigue contribution parameters may be represented as variables having values, so that the fatigue contribution parameters may be passed into other functions of the disclosure or incorporated into other aspects of the disclosure, for example, to create and update a fatigue profile (as described below).

Referring again to FIG. 9, at operation 906, method 900 includes identifying a fatigue source based on the fatigue level and the fatigue contribution data. In one embodiment, the fatigue source includes at least one of an activity type, an activity intensity, an activity duration, and an activity periodicity. For example, the fatigue source may include the activity type of running. The fatigue source may also be a combination of various activity data. To illustrate, the fatigue source may be the combination of running for a long activity duration and at a short activity periodicity. In an additional embodiment, the fatigue source may be identified by various aspects of the sleep data. In such an embodiment, the fatigue source may be the sleep duration, the sleep timing, the sleep quality, or the ambient light, or a combination thereof. Likewise, the various aspects of the location data and the calendar data, and combinations thereof, may constitute the fatigue source.

In one embodiment of the disclosure, the fatigue source is identified further based on user input. For example, the user may be provided several choices for fatigue source, from which the user may select one or more. These choices may be generated from historically identified fatigue sources or from a default library of fatigue sources. In addition, the user may enter the fatigue source manually. The user, in one embodiment, is prompted to provide the user input. The user may be prompted to provide the user input to aid in identifying the fatigue source when the fatigue source is not readily identifiable. The prompt for the user input may come in the form of a push notification, a text message, or other form, such as an in-application pop-up.

Figure 10:
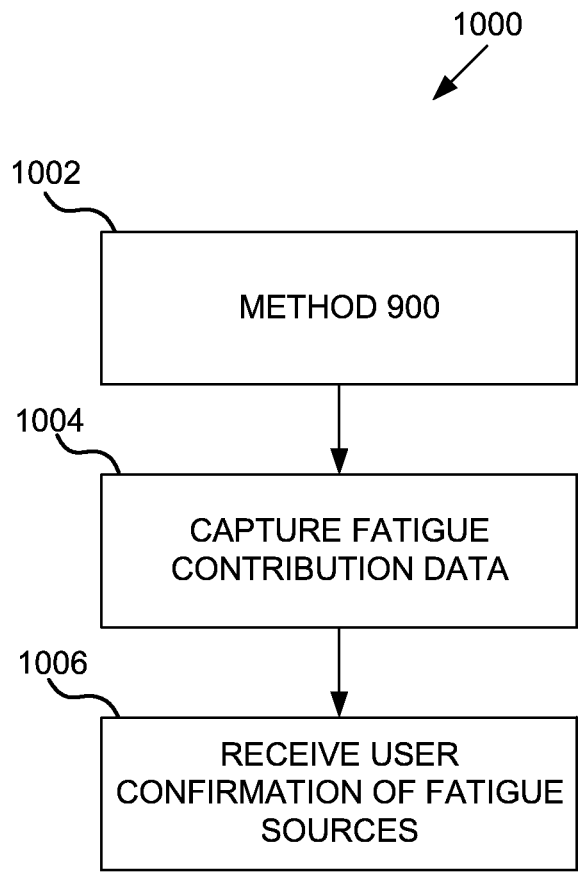
FIG. 10 is an operational flow diagram illustrating an example method for identifying fatigue sources including capturing fatigue contribution data and receiving user confirmation of fatigue sources.

FIG. 10 is an operational flow diagram illustrating example method 1000 for identifying fatigue sources. In one embodiment, apparatus 702, wristband 100, and electronic capsule 200 perform various operations of method 1000. Method 1000, in various embodiments, includes the operations of method 900. One embodiment of method 1000 involves capturing the fatigue contribution (e.g., at operation 1004). In such an embodiment, in addition to receiving the fatigue contribution data, method 1000 includes the monitoring operations described above (e.g., monitoring activity type, activity intensity, sleep duration, sleep quality, etc.) to capture the fatigue contribution.

At operation 1006, one embodiment of method 1000 involves receiving user confirmation of identified fatigue sources. In such an embodiment, the user confirmation serves as a check for the fatigue source identified at operation 906. In other instances, however, in addition to providing confirmation, the user provides information regarding the fatigue source. For example, the user may enter notes about why that particular fatigue source contributed to the user's fatigue level. To illustrate, the user may enter a note that says, "I ran a lot of hills on this run, compared to my normally flat runs, and that's why this was a particularly tiring run." The user may also provide notes about how multiple, identified fatigue sources combined to contribute to the user's fatigue level.

Figure 11:
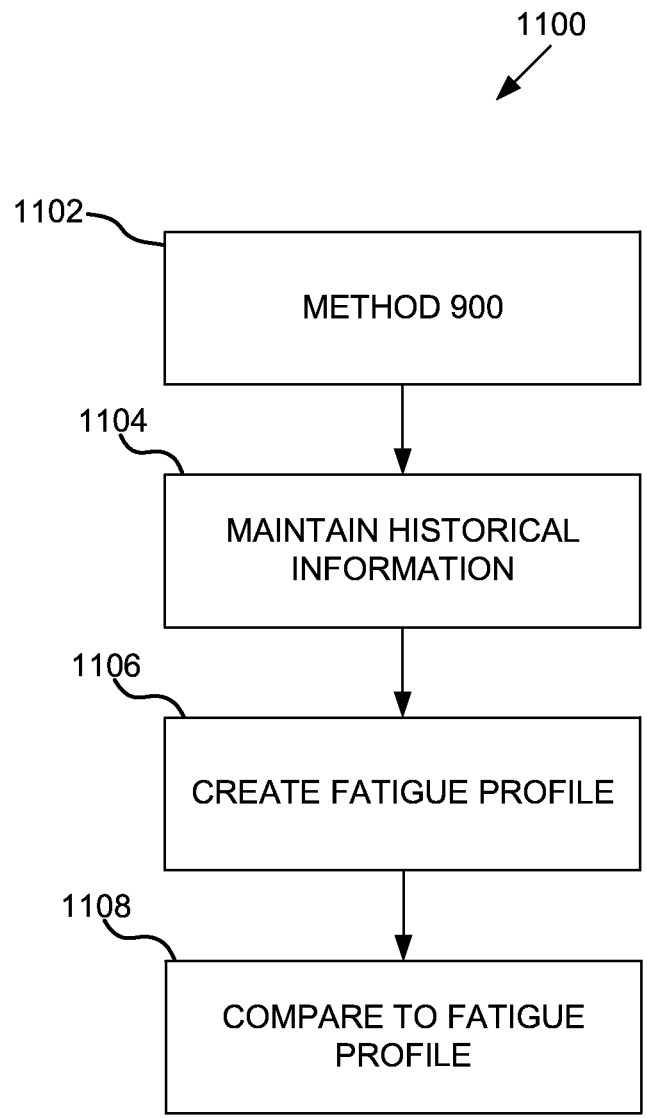
FIG. 11 is an operational flow diagram illustrating an example method for identifying fatigue sources including maintaining historical information, creating and updating a fatigue profile, and comparing to the fatigue profile.

FIG. 11 is an operational flow diagram illustrating example method 1100 for identifying fatigue sources. In one embodiment, apparatus 702, wristband 100, and electronic capsule 200 perform various operations of method 1100. Method 1100, in various embodiments, includes the operations of method 900. Method 1100 may also include the operations of method 1000. In one embodiment, at operation 1104, method 1100 involves maintaining historical information about the fatigue levels, the fatigue contribution data, the fatigue contribution parameters, and the fatigue sources identified. Such information may be stored and amassed in an archive as the information is collected. The archive may include tables for each type of historical information—to illustrate, the archive may include a table for historical fatigue level information, a table for historical fatigue contribution data, and so on.

A further embodiment of includes creating and updating a fatigue profile based on the historical information maintained in operation 1104, and comparing the fatigue level and the fatigue contribution data to the fatigue profile, as illustrated by operations 1106 and 1108 in FIG. 11. The fatigue profile may be based on historical information about one or more of the fatigue levels, the fatigue contribution data, the fatigue contribution parameters, or the fatigue sources identified. So, for example, the fatigue profile may include a range of fatigue levels that is typical for the user based on past measurements. For illustration, this range may be statistical—e.g., defined by standard deviations and the like.

Fatigue levels outside the user's typical range (e.g., a range of 40 to 60 for fatigue level may represent the 25th to 75th percentile range for the user), may be indicative of what the user's fatigue sources are. If, for example, the user's fatigue level on a particular day is outside the user's typical range (based on historical information), the fatigue contribution parameters leading up to that particular day may be likely candidates for the fatigue source. To illustrate: if, as indicated by the fatigue contribution data, the user's sleep duration was particularly low for several days preceding an unusually high fatigue level measurement, then the fatigue source likely would be the sleep duration, and may be identified as such. Method 1100 includes more complex scenarios, as will be recognized by one of ordinary skill in the art, including scenarios in which multiple fatigue contribution parameters are analyzed in identifying the fatigue source. Moreover, in some embodiments, multiple fatigue sources are identified.

One embodiment of the disclosure involves ranking multiple fatigue sources. When multiple fatigue sources are identified, the user may benefit from knowing the relative contribution of each identified fatigue source. Accordingly, multiple fatigue sources, once identified, may be ranked according to the amount these fatigue sources contribute to the fatigue level. The sources' relative contribution to the fatigue level may be determined using several methodologies.

For example, one methodology for determining sources' contribution to the fatigue level is using the comparing operation described above with respect to operation 1108. Certain of the fatigue contribution data, when compared to the fatigue profile, may represent relatively further deviations from the ranges of typical levels in the fatigue profile. To illustrate this methodology, upon detecting a particularly high fatigue level (e.g., 75 on a scale of 100), the fatigue contribution data may indicate that the user's sleep duration was below the 25th percentile for the user (e.g., 3 hours). Moreover, the fatigue contribution data may also indicate that the user had a particularly long or strenuous workout (e.g., high activity intensity or long activity duration), above the 75th percentile for the user. The sleep duration, the activity intensity, and the activity duration may each be identified as fatigue sources in this example. A comparison of each of these to the fatigue profile may show the relative amounts of deviation from the user's standard levels, and these deviations may be used to rank the sources' contribute to the fatigue level. Additional insight into the sources' contribution may be obtained by way of the archive. For example, the historical information may indicate that the user does not become fatigued due to low sleep durations. In such an example, the contribution of a low sleep duration may be weighted less relative to another fatigue source, and sleep duration may be ranked lower as a fatigue source.

Another methodology for ranking the contribution of multiple, identified fatigue sources may be based on default settings rather than the user's fatigue profile. For example, the default settings may include a default fatigue profile that is based on normative data gathered from large numbers of users or from publicly available information. The default fatigue profile may be used for comparison purposes in a fashion substantially similar to the user's fatigue profile, described above.

Yet another methodology for ranking the contribution of multiple, identified fatigue sources may be by user input. For example, once multiple fatigue sources are identified, the fatigue sources may be displayed to the user for manual ranking, and the user can rank the fatigue sources. To illustrate, the fatigue sources may be displayed on a touchscreen and the user may tap and drag the sources to arrange them vertically by perceived amount of fatigue contribution. One embodiment of the disclosure involves incorporating user-ranked fatigue source contributions into the user's fatigue profile. In other words, in such an embodiment, the method learns the user's self-evaluated fatigue sources.

In one embodiment, method 1100 includes displaying temporal trends in the historical information. As described above, the historical information may include the fatigue levels, the fatigue contribution parameters, and the fatigue sources. Displaying temporal trends in the historical information may include how the user's fatigue sources have changed over time, and how the fatigue sources have affected the user's fatigue level over time. Such a display may aid the user in identifying lifestyle choices for activity, rest, sleep, and work that lead to an optimal fatigue level (i.e., a fatigue level where the user is not too tired but not too rested). Moreover, such a display may aid the user in visually correlating how the user's historical choices have affected the user in terms of fatigue level.

Figure 12:
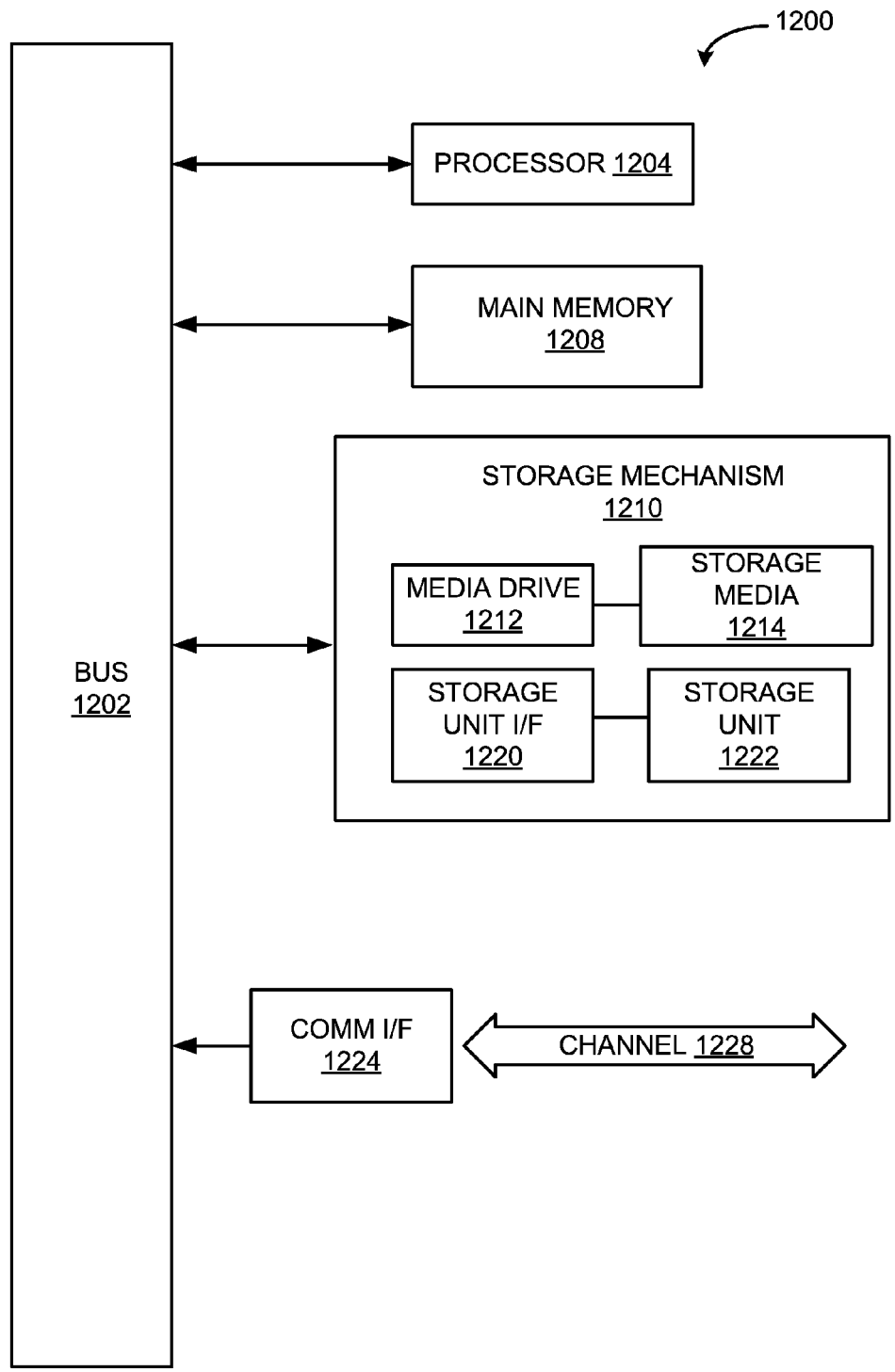
FIG. 12 illustrates an example computing module that may be used to implement various features of the systems and methods disclosed herein.

FIG. 12 illustrates an example computing module that may be used to implement various features of the systems and methods disclosed herein. In one embodiment, the computing module includes a processor and a set of computer programs residing on the processor. The set of computer programs is stored on a non-transitory computer readable medium having computer executable program code embodied thereon. The computer executable code is configured to detect a fatigue level. The computer executable code is further configured to receive fatigue contribution data. In addition, the computer executable code is configured to identify a fatigue source based on the fatigue level and the fatigue contribution data. One of ordinary skill in the art will appreciate that the computer executable code, in various embodiments, is configured to perform the various operations of the methods described herein. In various embodiments, at least a portion of the computer readable medium is embodied in a wearable sensor or a wearable device.

As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 12. Various embodiments are described in terms of this example-computing module 1200. After reading this description, it will become apparent to a person skilled in the relevant art how to implement the application using other computing modules or architectures.

Referring now to FIG. 12, computing module 1200 may represent, for example, computing or processing capabilities found within desktop, laptop, notebook, and tablet computers; hand-held computing devices (tablets, PDA's, smart phones, cell phones, palmtops, smart-watches, smart-glasses etc.); mainframes, supercomputers, workstations or servers; or any other type of special-purpose or general-purpose computing devices as may be desirable or appropriate for a given application or environment. Computing module 1200 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 1200 might include, for example, one or more processors, controllers, control modules, or other processing devices, such as a processor 1204. Processor 1204 might be implemented using a general-purpose or special-purpose processing engine such as, for example, a microprocessor, controller, or other control logic. In the illustrated example, processor 1204 is connected to a bus 1202, although any communication medium can be used to facilitate interaction with other components of computing module 1200 or to communicate externally.

Computing module 1200 might also include one or more memory modules, simply referred to herein as main memory 1208. For example, preferably random access memory (RAM) or other dynamic memory, might be used for storing information and instructions to be executed by processor 1204. Main memory 1208 might also be used for storing temporary variables or other intermediate information during execution of instructions to be executed by processor 1204. Computing module 1200 might likewise include a read only memory ("ROM") or other static storage device coupled to bus 1202 for storing static information and instructions for processor 1204.

The computing module 1200 might also include one or more various forms of information storage mechanism 1210, which might include, for example, a media drive 1212 and a storage unit interface 1220. The media drive 1212 might include a drive or other mechanism to support fixed or removable storage media 1214. For example, a hard disk drive, a solid state drive, a magnetic tape drive, an optical disk drive, a CD or DVD drive (R or RW), or other removable or fixed media drive might be provided. Accordingly, storage media 1214 might include, for example, a hard disk, a solid state drive, magnetic tape, cartridge, optical disk, a CD or DVD, or other fixed or removable medium that is read by, written to or accessed by media drive 1212. As these examples illustrate, the storage media 1214 can include a computer usable storage medium having stored therein computer software or data.

In alternative embodiments, information storage mechanism 1210 might include other similar instrumentalities for allowing computer programs or other instructions or data to be loaded into computing module 1200. Such instrumentalities might include, for example, a fixed or removable storage unit 1222 and a storage interface 1220. Examples of such storage units 1222 and storage interfaces 1220 can include a program cartridge and cartridge interface, a removable memory (for example, a flash memory or other removable memory module) and memory slot, a PCMCIA slot and card, and other fixed or removable storage units 1222 and storage interfaces 1220 that allow software and data to be transferred from the storage unit 1222 to computing module 1200.

Computing module 1200 might also include a communications interface 1224. Communications interface 1224 might be used to allow software and data to be transferred between computing module 1200 and external devices. Examples of communications interface 1224 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 1224 might typically be carried on signals, which can be electronic, electromagnetic (which includes optical) or other signals capable of being exchanged by a given communications interface 1224. These signals might be provided to communications interface 1224 via a channel 1228. This channel 1228 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 1208, storage unit 1220, media 1214, and channel 1228. These and other various forms of computer program media or computer usable media may be involved in carrying one or more sequences of one or more instructions to a processing device for execution. Such instructions embodied on the medium are generally referred to as "computer program code" or a "computer program product" (which may be grouped in the form of computer programs or other groupings). When executed, such instructions might enable the computing module 1200 to perform features or functions of the present application as discussed herein.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

While various embodiments of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present disclosure should not be limited by any of the above-described exemplary embodiments.

What is claimed is:

1. A system for identifying fatigue sources for a user, comprising:
    a processor;
    a first sensor and one or more second sensors, wherein at least one of the one or more second sensors is a movement monitoring device configured to detect movement of the user's body; and
    at least one computer program residing on the processor, wherein the at least one computer program is stored on a non-transitory computer readable medium having computer executable program code embodied thereon, the computer executable program code executed by the processor and configured to:
    detect a fatigue level for the user from the first sensor when the first sensor is worn by the user;
    receive fatigue contribution data for the user from the one or more second sensors when the one or more second sensors are worn by the user, wherein the fatigue contribution data comprises data of fatigue contribution parameters, and wherein the fatigue contribution data comprises activity data from one or more hours prior to the detection of the fatigue level of the user;
    determine a relative contribution of each of a plurality of fatigue sources to the fatigue level of the user based on the received fatigue contribution data, wherein the relative contribution of at least one fatigue source is derived from the fatigue contribution data received from the movement monitoring device;
    identify a primary fatigue source for the user out of the plurality of fatigue sources based on the relative contribution of each of the plurality of fatigue sources to the fatigue level of the user, wherein the identify the primary fatigue source for the user out of the plurality of fatigue source comprises ranking the plurality of fatigue sources, wherein the processor is configured to maintain historical information about the fatigue levels, the fatigue contribution parameters, and the fatigue sources to create and update a fatigue profile for the user based on the historical information; and
    display the primary fatigue source for the user on a screen, wherein the display includes a feature for allowing a user to confirm the identified primary fatigue source.

2. The system of claim 1, wherein the activity data is associated with at least one of an activity type, an activity intensity, an activity duration, and an activity periodicity.

3. The system of claim 1, wherein the fatigue contribution data comprises sleep data, and wherein the sleep data is associated with at least one of a sleep duration, a sleep timing, a sleep quality, and an ambient light.

4. The system of claim 1, wherein the fatigue contribution data comprises location data.

5. The system of claim 4, wherein the location data is associated with at least one of a GPS location, an altitude, and an ambient temperature.

6. The system of claim 1, wherein the fatigue contribution data comprises calendar data.

7. The system of claim 1, wherein the fatigue source comprises at least one of an activity type, an activity intensity, an activity duration, and an activity periodicity.

8. The system of claim 1, wherein
    the identifying the primary fatigue source for the user further comprises determining deviations of different fatigue contribution parameters from typical ranges for the different respective fatigue contribution parameters based on the fatigue profile for the user.

9. A method for identifying fatigue sources for a user using an identifying fatigue source system comprising a processor and at least one computer program residing on the processor, wherein the at least one computer program is stored on a non-transitory computer readable medium having computer executable program code embodied thereon, the computer executable program code executed by the processor to perform method steps, comprising:
    detecting a fatigue level for the user from a first sensor when the first sensor is worn by the user;
    receiving fatigue contribution data for the user from one or more second sensors when the one or more second sensors are worn by the user, wherein at least one of the one or more second sensors is a movement monitoring device configured to detect movement of the user's body, wherein the fatigue contribution data comprises data of fatigue contribution parameters; and wherein the fatigue contribution data comprises activity data from one or more hours prior to the detecting the fatigue level for the user;
    determining a relative contribution of each of a plurality of fatigue sources to the fatigue level of the user based on the received fatigue contribution data, wherein the relative contribution of at least one fatigue source is derived from the fatigue contribution data received from the movement monitoring device;
    identifying a primary fatigue source for the user out of the plurality of fatigue sources based on the relative contribution of each of the plurality of fatigue sources to the fatigue level of the user, wherein the identifying the primary fatigue source for the user out of the plurality of fatigue source comprises ranking the plurality of fatigue sources, wherein the processor is configured to maintain historical information about the fatigue levels, the fatigue contribution parameters, and the fatigue sources to create and update a fatigue profile for the user based on the historical information;
    displaying the primary fatigue source for the user on a screen,
    wherein the display includes a feature for allowing a user to confirm the identified primary fatigue source; and
    adjusting a lifestyle of the user based on the identified primary fatigue source.

10. The method of claim 9,
wherein the identifying the primary fatigue source for the user further comprises determining deviations of different fatigue contribution parameters from typical ranges for the different respective fatigue contribution parameters based on the fatigue profile for the user.

* * * * *